US00PP24071P3

(12) United States Plant Patent
Meilland

(10) Patent No.: US PP24,071 P3
(45) Date of Patent: Dec. 10, 2013

(54) FLORIBUNDA ROSE PLANT NAMED 'MEINOPLIUS'

(50) Latin Name: *Rosa hybrida*
Varietal Denomination: Meinoplius

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 94 days.

(21) Appl. No.: 13/374,720

(22) Filed: Jan. 10, 2012

(65) Prior Publication Data

US 2013/0160171 P1 Jun. 20, 2013

(30) Foreign Application Priority Data

Dec. 14, 2011 (EM) ..... 2011/3077

(51) Int. Cl.
*A01H 5/00* (2006.01)

(52) U.S. Cl.
USPC ..... Plt./148; Plt./141

(58) Field of Classification Search
USPC ..... Plt./141, 148
See application file for complete search history.

(56) References Cited

PUBLICATIONS

Translation for Internet Retrieval on Jun. 5, 2013 "Floks Catalog" www.floks.by/catalog/all/3297 (4 pages total).*

* cited by examiner

*Primary Examiner* — Susan McCormick Ewoldt
(74) *Attorney, Agent, or Firm* — Buchanan Ingersoll & Rooney PC

(57) ABSTRACT

A new and distinct variety of Floribunda rose plant is provided that abundantly forms on a substantially continuous basis attractive double red-purple blossoms having a lighter coloration on the under surface. The vegetation is strong and a compact bushy growth habit is displayed. Exceptional resistance to common rose diseases has been observed. The plant is well suited for providing distinctive attractive ornamentation in the landscape.

1 Drawing Sheet

Botanical/commercial classification: *Rosa hybrida*/Floribunda Rose Plant.
Varietal denomination: Cv. Meinoplius.

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was the 'Meihatoil' variety (non-patented in the United States). The male parent (i.e., the pollen parent) was the product of the 'Korimro' variety (non-patented in the United States). The parentage of the new variety can be summarized as follows:

'Meihatoil'×'Korimro'.

The seeds resulting from the above pollination were sown and small plants were obtained which were physically and biologically different from each other. Selective study resulted in the identification of a single plant of the new variety.

It was found that the new Floribunda rose plant of the present invention:

(a) forms strong vegetation,
(b) forms a bushy compact growth habit,
(c) forms in abundance on a substantially continuous basis attractive small double red-purple blossoms having a lighter coloration on the under surface,
(d) displays attractive green foliage with a glossy aspect on the upper surface, (e) exhibits exceptional resistance to common rose diseases, and
(g) is well suited for providing distinctive attractive ornamentation in the landscape.

The new variety well meets the needs of the horticultural industry and can be grown to advantage in parks and gardens. Blossoming commonly commences early in the season.

The new variety can be readily distinguished from its ancestors. For instance, 'Meihatoil' variety forms dissimilar yellow blossoms. The 'Korimro' variety forms dissimilar single blossoms and lacks a propensity for repeat blooming.

The new variety additionally can be readily distinguished from the 'Meidomonac' variety (U.S. Plant Pat. No. 5,105) and the 'Meisylpho' variety (non-patented in the United States). The 'Meidomonac' variety displays a considerably taller growth habit and lacks a petal color change on the under surface. The 'Meisylpho' variety forms larger flowers and also lacks a petal color change on the under surface.

The new variety has been found to undergo asexual propagation at Le Cannet des Maures, Var, France, by a number of routes, including budding, grafting, and the use of cuttings. The plant grows well on its own roots. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meinoplius', and sometimes has been identified as 'Lovely Pink'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately one year of age and were observed during June while growing on their own roots outdoors at Le Cannet des Maures, Var, France. Standard colors are presented at the bottom of the photograph for comparison.

FIG. 3 illustrates a specimen of a floral bud at the further opening of the sepals;

FIG. 4 illustrates a specimen of a floral bud at the opening of the petals;

FIG. 5 illustrates a specimen of a flower in the course of opening;

FIG. 17 illustrates a specimen of a cluster of buds, and the opening flowers.

DETAILED BOTANICAL DESCRIPTION

Figures 1, 2, 6, 7, 8, 9, 10, 11, 12, 13, 14, 15, 16:
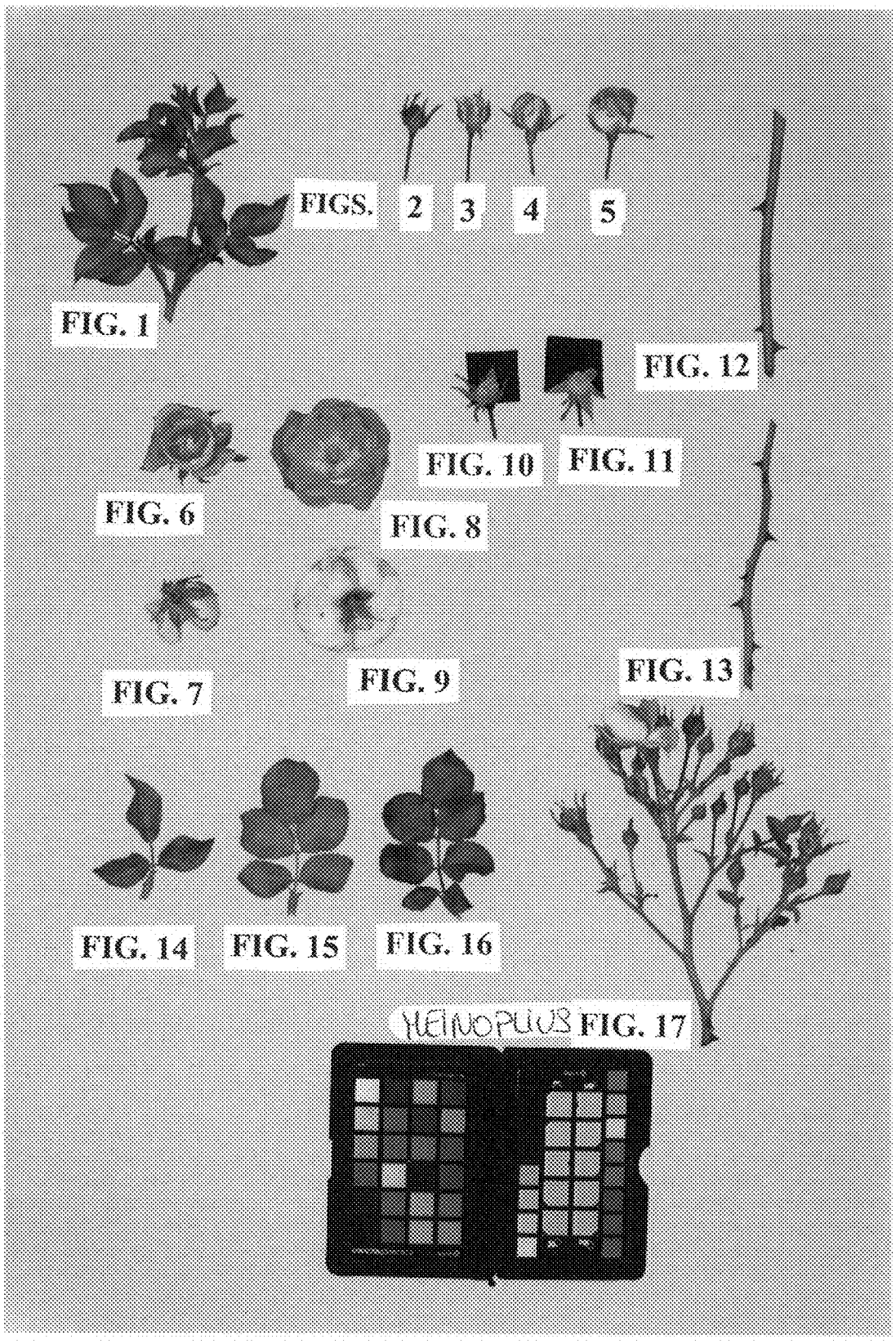
FIG. 1 illustrates a specimen of a young shoot.
FIG. 2 illustrates a specimen of a floral bud at the opening of the sepals.
FIG. 6 illustrates a specimen of an open flower-plan view-obverse.
FIG. 7 illustrates a specimen of an open flower-plan view-reverse.
FIG. 8 illustrates a specimen of a fully open flower-plan view-obverse.
FIG. 9 illustrates a specimen of a fully open flower-plan view-reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a flowering stem.
FIG. 13 illustrates a specimen of a main branch.
FIG. 14 illustrates a specimen of a leaf with 3 leaflets-plan view-upper surface.
FIG. 15 illustrates a specimen of a leaf with 5 leaflets-plan view-under surface.
FIG. 16 illustrates a specimen of a leaf with 7 leaflets-plan view-upper surface.

The chart used in the identification of the colors is that of The Royal Horticultural Society (R.H.S. Colour Chart-1995 Edition or equivalent) except where ordinary color terms are utilized. Such common color terms are to be accorded their customary dictionary significance. The description is based upon the observation during May of plants of the new variety at an age of approximately one year while growing on their own roots outdoors at Le Cannet des Maures, Var, France.

Class: Floribunda.

Plant:

*Growth habit.*—Bushy.

*Height.*—Approximately 35 to 40 cm on average.

*Width.*—Approximately 40 cm on average.

Branches:

*Color.*—Young stems: near Yellow-Green Group 144B. Adult wood: near Yellow-Green Group 144A.

*Stem number.*—Commonly approximately 4 to 6 on average.

*Stem length.*—Commonly approximately 30 to 35 cm on average.

*Thorns.*—On young stems: commonly absent. On adult stems: configuration: generally upright and slightly concave on the under surface with an ovate base. smaller prickles: over a stem length of 10 cm approximately 5 having a length of approximately 0.7 cm, and a coloration of near Red Group 39B and 39C. longer prickles: over a stem length of 10 cm approximately 11 having a length of approximately 0.8 cm, and a coloration of Greyed-Orange Group 166C.

Leaves:

*Overall appearance.*—Dense, attractive dark green.

*Size.*—Approximately 7.5 cm in length on average, and approximately 6 cm in width on average for a five-leaflet leaf.

*Leaflets.*—Shape: generally oval. number: 3, 5 (most often) and 7. apex: acuminate. base: obtuse. Size: the terminal leaflets commonly are approximately 3 cm in length on average, and approximately 2.8 cm in width on average. Serration: small and single. Venation: substantially regular around a central main vein, commonly near Green Group 137B on the upper surface and near Yellow-Green Group 146B on the under surface. Texture: firm and leathery. Color: young foliage: near Green Group 137A on the upper surface, and near Yellow-Green Group 146B on the under surface. mature foliage: near Green Group 137A on the upper surface, and near Yellow-Green Group 146B on the under surface.

*Stipules.*—General appearance: adnate, pectinate, and rather broad. Length: approximately 1.8 cm on average. Width: approximately 0.6 cm on average. Color: near Yellow-Green Group 146D on the upper surface, and near Yellow-Green Group 146B on the under surface.

*Petioles.*—Length: commonly approximately 2 cm on average for the terminal leaflet. Texture: non-glandular on the upper surface, and commonly with a few prickles on the under surface. Color: near Yellow-Green Group 146D on the upper and under surfaces.

*Rachis.*—Color: near Yellow-Green Group 146D on the upper surface, and near Yellow-Green Group 146B on the under surface.

Inflorescence:

*Number of flowers.*—Commonly three to ten or more per stem. On Jun. 5, 2013, seventy-five flowers were observed on a one-year-old plant, and on Sep. 5, 2013, no flowers were present.

*Peduncle.*—Approximately 3 cm in length on average, approximately 5 mm in diameter on average, smooth in texture, and commonly near Yellow-Green Group 146B in coloration.

*Sepals.*—Tomentose on upper surface, smooth on under surface, generally upright, commonly approximately 1.5 cm in length on average, approximately 0.7 cm in width on average at the widest point, near Yellow-Green Group 148C on the upper surface, and near Yellow-Green Group 147B on the under surface.

*Buds.*—Shape: generally conical. Size: small. Length: approximately 1.2 cm on average. Width: approximately 0.9 cm at the widest point on average. Color: upper surface: near Red-Purple Group 66D suffused with near Red-Purple Group 66A. under surface: near Red-Purple Group 62D.

*Flower.*—Diameter approximately 7 cm on average when fully open. Depth: approximately 2.5 cm when fully open. Shape: cup-shaped. Color (in course of opening): upper side: near Red-Purple Group 68D suffused with near Red-Purple Group 66C, and with a spot of near Yellow Group 2D at the base. under side: near Red-Purple Group 62D, and with a spot of White Group 155D at the base. Color (when fully open): upper side: near Red-Purple Group 68D suffused with Red-Purple Group 68A, and with a spot of Yellow Group 2D at the base. under side: near Red-Purple Group 65D, and with a spot of near White Group 155D at the base. Fragrance: none observed. Petal number: commonly approximately 55 on average under normal growing conditions. Petal shape: with a rounded tip and an obtuse base. Petal size: commonly approximately 2.5 cm on average in length and width. Petal arrangement: imbricated and without petaloids. Petal substance: firm and leathery. Petal drop: good with the petals commonly detaching cleanly before drying. Stamen number: approximately 18 on average. Anthers: regularly arranged around the styles, approximately 1 mm in size on average, and near Orange Group 24D in coloration. Filaments: commonly approximately 6 mm in size on average, and near Yellow Group 2D in coloration. Pistils: commonly approximately 33 on average. Styles: approximately 1 mm in size on average, and commonly near Red Group 53D in coloration. Stigmas: commonly approximately 7 mm in size on average, and commonly near Yellow Group 2D in coloration. Receptacle: shape: funnel-shaped. length: approximately 5 mm on average. width: approximately 5 mm at widest point on average. texture: smooth. color: near Yellow-Green Group 144D.

Development:

*Vegetation.*—Strong.

*Blooming.*—Early season, very abundant, and substantially continuous.

*Tolerance to diseases.*—Very good for common rose diseases during observations to date.

Plants of the new 'Meinoplius' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) forms strong vegetation, (b) forms a bushy compact growth habit, (c) forms in abundance on a substantially continuous basis attractive small double red-purple blossoms having a lighter coloration on the under surface, (d) displays attractive green foliage with a glossy aspect on the upper surface, (e) exhibits exceptional resistance to common rose diseases, and (g) is well suited for providing distinctive attractive ornamentation in the landscape;

substantially as shown and described.

* * * * *

YLEINOPUUS FIG. 17